(12) United States Patent
Mamelak et al.

(10) Patent No.: US 8,778,301 B2
(45) Date of Patent: Jul. 15, 2014

(54) GAMMA-HYDROXYBUTYRATE COMPOSITIONS CONTAINING CARBOHYDRATE, LIPID OR AMINO ACID CARRIERS

(75) Inventors: Mortimer Mamelak, Toronto (CA); William C. Houghton, St. Paul, MN (US); Dayton T. Reardan, Excelsior, MN (US); Brian L. Miller, Eden Prairie, MN (US)

(73) Assignee: Orphan Medical, Inc., Palo Alto, CA (US)

( * ) Notice: Subject to any disclaimer, the term of this patent is extended or adjusted under 35 U.S.C. 154(b) by 0 days.

(21) Appl. No.: 12/465,069

(22) Filed: May 13, 2009

(65) Prior Publication Data

US 2009/0215890 A1 Aug. 27, 2009
US 2010/0022643 A2 Jan. 28, 2010

Related U.S. Application Data

(62) Division of application No. 11/183,482, filed on Jul. 18, 2005, now Pat. No. 7,572,605, which is a division of application No. 10/381,224, filed as application No. PCT/US01/29569 on Sep. 21, 2001, now Pat. No. 7,015,200.

(60) Provisional application No. 60/234,720, filed on Sep. 22, 2000.

(51) Int. Cl.
| | | |
|---|---|---|
| *A61K 51/08* | (2006.01) | |
| *C12P 13/04* | (2006.01) | |
| *C07C 233/49* | (2006.01) | |
| *C07C 229/24* | (2006.01) | |
| *C07C 69/67* | (2006.01) | |
| *C07C 233/47* | (2006.01) | |
| *C07C 69/675* | (2006.01) | |
| *C07C 229/36* | (2006.01) | |
| *C07H 13/04* | (2006.01) | |
| *C07C 229/22* | (2006.01) | |

(52) U.S. Cl.
CPC ............ *C07C 69/675* (2013.01); *C07C 233/49* (2013.01); *C07C 229/24* (2013.01); *C07C 69/67* (2013.01); *C07C 233/47* (2013.01); *C07C 229/36* (2013.01); *C07H 13/04* (2013.01); *C07C 229/22* (2013.01)
USPC .......... 424/1.69; 435/106; 435/109; 435/110; 426/23

(58) Field of Classification Search
CPC .................................................. A61K 51/088
USPC ............. 424/1.69; 435/106, 109, 110; 426/23
See application file for complete search history.

(56) References Cited

U.S. PATENT DOCUMENTS

| | | |
|---|---|---|
| 4,599,355 A | 7/1986 | Kluger et al. |
| 4,738,985 A | 4/1988 | Kluger et al. |
| 4,755,619 A | 7/1988 | Creighton et al. |
| 5,753,708 A | 5/1998 | Koehler et al. |
| 7,015,200 B2 | 3/2006 | Mamelak et al. |
| 2005/0250848 A1 | 11/2005 | Mamelak et al. |
| 2013/0324759 A1 | 12/2013 | Mamelak et al. |

FOREIGN PATENT DOCUMENTS

| | | |
|---|---|---|
| EP | 0442850 | 8/1991 |
| WO | WO-95/14476 | 6/1995 |

OTHER PUBLICATIONS

"U.S. Appl. No. 11/183,482, Response filed Nov. 19, 2008 to Non-Final Office Action mailed Aug. 20, 2008", 8 pgs.
"U.S. Appl. No. 11/183,482, Notice of Allowance mailed Apr. 8, 2009", 9 pgs.
"U.S. Appl. No. 11/183,482 Non-Final Office Action Mailed Aug. 20, 2008", OARN, 9 Pgs.
Barrett, A. G. M, et al., "Redox Glycosidation: A New Strategy for Disaccharide Synthesis", *J. Am. Chem. Soc.*, 111 (4), (1989), 1392-1396.
Bedard, M A, "Nocturnal γ-Hydroxybutyrate—Effect on Periodic Leg Movements and Sleep Organization of Narcoleptic Patients", *Clin Neuropharmacol.*, 12(1), (Feb. 1989), 29-36.
Broughton, R, "Effects of nocturnal gamma-hydroxybutyrate on sleep/waking patterns in narcolepsy-cataplex", Canadian Journal of Neurological Sciences. 7(1), (Feb. 1980), 23-31.
Carter Snead, O., et al., "Ontogeny of Gamma-Hydroxybutyric Acid. Regional Concentration in Developing Rat, Monkey and Human Brain", *Brain Res.*, 227(4), (1981), 579-589.
Gallimberti, L, et al., "Clinical efficacy of gamma-hydroxybutyric acid in treatment of opiate withdrawal", *Eur. Arch. Psychiatry Clin. Neurosci.*, 244 (3), (1994), 113-4.
Gallimberti, L, "Gamma-Hydroxybutric Acid in the Treatment of Alcohol Dependence: A Double-Blind Study", *Alcohol Clin. Exp. Res.*, 16(4), (1992), 673-676.
Gallimberti, L, "Gamma-hydroxybutyric Acid for Treatment of Alcohol Withdrawal Syndrome", *Clinical Pharmacology*, 2(8666), (1989), 787-789.
Gallimberti, L, et al., "Gamma-hydroxybutyric acid for treatment of opiate withdrawal syndrome", *Neuropsychopharmacology*. 9(1), (Aug. 1993), 77-81.
Gerra, G, et al., "Flumazenil effects on growth hormone response to gamma-hydroxybutyric acid", *Int. Clin. Psychopharmacol.*, 9 (3), (Sep. 1994), 211-5.

(Continued)

Primary Examiner — Brandon Fetterolf
Assistant Examiner — Everett White
(74) Attorney, Agent, or Firm — Schwegman Lundberg & Woessner, P.A.

(57) ABSTRACT

The present invention provides compositions comprising at least one GHB moiety bonded to at least one physiologically compatible carrier molecule. The compositions can enhance the uptake of the drug, deliver effective therapeutic doses in a time-delayed fashion, or can target specific organs.

15 Claims, 5 Drawing Sheets

(56) References Cited

OTHER PUBLICATIONS

Gessa, G L, "Gamma-hydroxybutyric Acid in the Treatment of Alcohol Dependence", *Clin. Neuropharm.*, 15 Suppl 1 Pt A, (1992), 303a-304a.

Grove-White, I G, "Critical Flicker Frequency after Small Doses of Methohexitone, Diazepam and Sodium 4-Hydroxybutyrate", *Brit. J. Anaesth*, 43(2), (1971), 110-2.

Hasenbos, M A, "Anaesthesia for bullectomy. A technique with spontaneous ventilation and extradural blockade", *Anaesthesia*, 40(10), (1985), 977-980.

Hoes, M J, "Gamma-hydroxybutyric acid as hypnotic. Clinical and pharmacokinetic evaluation of gamma-hydroxybutyric acid as hypnotic in man", *Encephale*, 6(1), (1980), 93-99.

Laborit, H., "Gamma-Hydroxybutyrate, Succinic Semialdehyde and Sleep", *Laboratoire d'Eutonologie*, (1973), 257-274.

Ladinsky, Herbert, "Mode of Action of Gamma-Butyrolactone on the Central Cholinergic System", *Naunyn-Schmiedeberg's Arch. Pharmacol.*, 322, (1983), 42-48.

Lammers, G J, "Gammahydroxybutyrate and Narcolepsy: A Double-Blind Placebo-Controlled Study", *Sleep*, 16(3), (1993), 216-220.

Lapierre, O., "The Effect of Gamma-Hydroxybutyrate on Nocturnal and Diurnal Sleep of Normal Subjects: Further Considerations on REM Sleep-Triggering Mechanisms", *Sleep*, 13, (1990), 24-30.

Lee, C R, "Evidence for the B-Oxidation of Orally Administered 4-Hydroxybutyrate in Humans", *Biochemical Medicine*, 17g, (1977), 284-291.

Mamelak, M, et al., "Narcolepsy: a family study", *Biological Psychiatry*. 14(5), (Oct. 1979), 821-34.

Mamelak, M, "Sleep-Inducing Effects of Gammahydroxybutyrate", *The Lancet*, 2(7824), (1973), 328-329.

Mamelak, Mortimer, "The Effects of Gamma-Hydroxybutyrate on Sleep", *Biological Psychiatry*, 12(2), (1977), 273-288.

Oyama, T, et al., "Effects of neuroleptanaesthesia on plasma levels of growth hormone and insulin", *Br. J. Anaesth.*, 42 (12), (Dec. 1970), 1105-12.

Palatini, P, "Dose Dependent Absorption and Elimination of Gamma-Hydroxybutyric Acid in Healthy Volunteers", *Eur. J. Clin. Pharmacol.*, 45(4), (1993), 353-356.

Scharf, M B, "The Effects and Effectiveness of y-Hydroxybutyrate in Patients with Narcolepsy", *J. Clin. Psychiatry*, 46(6), (1985), 222-225.

Scharf, M. B., "Current Pharmacologic Management of Narcolepsy", *American Family Physician*, 38(1), (Jul. 1988), 143-148.

Scrima, L, "The Effects of Y-Hydroxybutyrate on the Sleep of Narcolepsy Patients: A Double-Blind Study", *Sleep*, 13(6), (1990), 479-490.

Series, F, "Effects of Enhancing Slow-Wave Sleep by Gamma-Hydroxybutyrate on Obsturctive Sleep Apnea", *Am. Rev. Respir. Dis.*, 145(6), (1992), 1378-1383.

Stock, G, "Increase in brain dopamine after axotomy or treatment with Gammahydroxybutyric acid due to elimination of the nerve impulse flow", *Naunyn-Schmiedeberg's Arch. Pharmacol.*, 278(4) (1973), 347-361.

Strong, A J, "gamma-Hydroxybutyric acid and intracranial pressure", *The Lancet*, 1(8389), (1984), 1304.

Yamada, Y., "Effect of Butyrolactone and Gamma-Hydroxybutyrate on the EEG and Sleep Cycle in Man", *Electroenceph. clin. Neurophysiol.*, 22, (1967), 558-562.

"U.S. Appl. No. 10/381,224, 312 Amendment filed Jun. 20, 2005", 4 pgs.

"U.S. Appl. No. 10/381,224, Non Final Office Action mailed Oct. 6, 2004", 10 pgs.

"U.S. Appl. No. 10/381,224, Notice of Allowance mailed Mar. 22, 2005", 6 pgs.

"U.S. Appl. No. 10/381,224, Preliminary Amendment filed Mar. 21, 2008", 3 pgs.

"U.S. Appl. No. 10/381,224, PTO Response to 312 Amendment mailed Dec. 30, 2005", 2 pgs.

"U.S. Appl. No. 10/381,224, Response filed Jan. 4, 2005 to Non Final Office Action mailed Oct. 6, 2004", 8 pgs.

"U.S. Appl. No. 10/381,224, Supplemental Preliminary Amendment filed Dec. 10, 2003", 10 pgs.

"U.S. Appl. No. 11/183,482, Response filed May 30, 2008 to Restriction Requirement mailed Apr. 30, 2008", 7 pgs.

"U.S. Appl. No. 11/183,482, Restriction Requirement mailed Apr. 30, 2008", 7 pgs.

"U.S. Appl. No. 13/897,748, Non Final Office Action mailed Oct. 4, 2013", 6 pgs.

GLUTAMIC ACID

TYROSINE

ASPARTIC ACID

GAMMA-HYDROXYBUTYRATE COMPOSITIONS CONTAINING CARBOHYDRATE, LIPID OR AMINO ACID CARRIERS

CROSS-REFERENCE TO RELATED APPLICATIONS

This application is a divisional of U.S. application Ser. No. 11/183,482, filed on Jul. 18, 2005 (U.S. Pat. No. 7,572,605), which is a divisional of U.S. application Ser. No. 10/381,224, filed on Mar. 21, 2003 (U.S. Pat. No. 7,015,200), which is a U.S. National Stage filing under 35 U.S.C. 371 from International Application No. PCT/US01/29569, filed Sep. 21, 2001 and published in English as WO 02/24715 A2 on Mar. 28, 2002, which claims priority from U.S. Provisional Application Ser. No. 60/234,720 filed on Sep. 22, 2000, the disclosures of which applications and publication are incorporated by reference herein in their entirety.

BACKGROUND OF THE INVENTION

Gamma-hydroxybutyric acid or "gamma-hydroxybutyrate" (GHB) is an endogenous compound with hypnotic properties that is found in many human body tissues. GHB is present, for example, in the mammalian brain, the human nervous system and other tissues. The extraordinary range of the pharmacological effects of GHB or its salts has attracted scientific attention for more than three decades. For example, GHB has been found to have tissue-protective effects in animals and man in many different organs including brain, liver, lung, heart, kidney, gut and pancreatic B cells. In brain the highest GHB concentration is found in the hypothalamus and basal ganglia and GHB is postulated to function as a neurotransmitter (Snead and Morley, 1981). The neuropharmacologic effects of GHB include increases in brain dopamine, depression of glucose utilization but not oxygen consumption in the brain, and hypothermia. GHB is converted to succinate and then metabolized via the Krebs cycle. Clinical trials have shown that GHB increases delta sleep and improves the continuity of sleep (Ladinsky et al., 1983; Stock et al., 1973; Laborit, 1973; Lapierre et al., 1990; Yamada et al., 1967; Grove-White and Kelman, 1971; Scharf, 1985).

In healthy human volunteers, low doses (about 30 mg/kg) of GHB monosodium salt (sodium oxybate) promote a normal sequence of NREM and REM sleep lasting about 2-3 hours. These low doses also can induce REM and slow wave sleep and, in contrast to the hypnotics in common use, without the development of tolerance to these sleep-inducing effects in time. In addition, GHB increases total sleep time and REM sleep, and it decreases REM latency (Mamelak et al., 1973; Yamada et al., 1967; Bedard et al., 1989), reduces sleep apnea (Series et al., 1992; Scrima et al., 1987), and improves general anesthesia (Hasenbos and Gielen, 1985).

Studies by R. Broughton and M. Mamelak, *Can. J. Neur. Sci.*, 7, 23 (1980), L. Scrima et al., *Sleep*, 13, 479 (1990), and M. B. Scharf et al., *Am. Fam. Phys.*, 143 (July 1988) have evaluated the effects of GHB in the treatment of narcolepsy. The results of these studies confirm that GHB treatment substantially reduces the signs and symptoms of narcolepsy (e.g., daytime sleepiness, cataplexy, sleep paralysis and hypnagogic hallucinations).

GHB has several clinical applications other than the treatment of sleep disorders. GHB has been reported to reduce alcohol craving, the number of daily drinks consumed, and the symptoms of alcohol withdrawal in patients (Gallimberti et al., 1989; Gallimberti et al., 1992; Gessa et al., 1992). GHB has been used to decrease the symptoms of opiate withdrawal, including both heroin and methadone withdrawal (Gallimberti et al., 1994; Gallimberti et al., 1993). It has analgesic effects that make it suitable as a pain reliever (U.S. Pat. No. 4,393,236). Intravenous administration of GHB has been reported to reduce intracranial pressure in patients (Strong, A. 1984). Also administration of GHB was reported to increase growth hormone levels in patients (Gerra et al., 1994; Oyama et al., 1970). GHB is also an effective therapeutic agent for the treatment of chronic fatigue syndrome and fibromyalgia (Scharf, U.S. Pat. No. 5,990,162).

Unfortunately, the efficacy of GHB is limited by the high doses required to produce a therapeutic effect and by its short duration of action. Thus, a need exists for GHB compositions that can enhance the uptake of the drug, deliver effective therapeutic doses in a time-delayed fashion, and target specific organs.

SUMMARY OF THE INVENTION

The present invention provides a compound of formula (I):

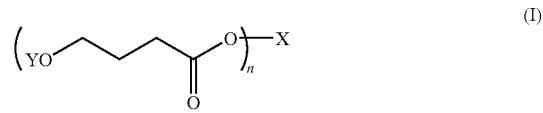

wherein Y is H or a hydroxyl-protecting group, X is the residue of a carbohydrate and n has a value of 1 to the number of available hydroxyl groups in said carbohydrate, or a pharmaceutically acceptable salt thereof.

Preferably, X is a saccharide, and Y is H, a $(C_4$-$C_6)$acetal, $(C_1$-$C_5)$acyl or $(C_1$-$C_5)$alkyl.

Preferred carbohydrates are water-soluble or water-dispersible. In yet another preferred embodiment of the invention, X is the residue of a monosaccharide, the residue of a disaccharide or the residue of a polysaccharide.

In such compounds, the monosaccharide, disaccharide or polysaccharide can contain at least one CHOH—CHOH residue that is protected as an acetal or ketal.

Examples of compounds of formula (I) include 1,2,3,4,6-pentakis(4-hydroxy-butyroyl)hexanose; 6-(4-hydroxy-butyroyl)hexanose and 1,2,3,4,6-pentakis(4-acetoxybutyroyl) hexanose.

In a further preferred embodiment of the compound of formula (I), X is the residue of a chemically-modified cellulose. Useful chemically-modified cellulose compositions include water-soluble or water-dispersible celluloses such as hydroxypropyl-methylcellulose, hydroxypropylcellulose or hydroxyethylcellulose.

Further provided by the present invention is a compound of formula (II):

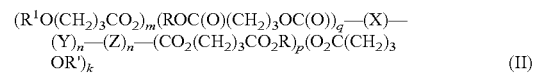

$$(R^1O(CH_2)_3CO_2)_m(ROC(O)(CH_2)_3OC(O))_q\text{—}(X)\text{—}\\(Y)_n\text{—}(Z)_n\text{—}(CO_2(CH_2)_3CO_2R)_p(O_2C(CH_2)_3\\OR')_k \qquad (II)$$

wherein R' is H or a hydroxyl protecting group, R' is H, $(C_1$-$C_4)$alkyl or benzyl, X and Z are each residues of a hydroxy group-containing amino acid or a bis(carboxy) amino acid, Y is a moiety covalently linking X and Z, n is 0-1, m and k are 0 to the number of available OH groups on X and Z, q and p are 0 to the number of available $CO_2$ groups on X and Z, with the proviso that m and q are not both zero and p and k are not both zero, or a pharmaceutically acceptable salt thereof.

An embodiment of the compound of formula II is a compound of formula (III):

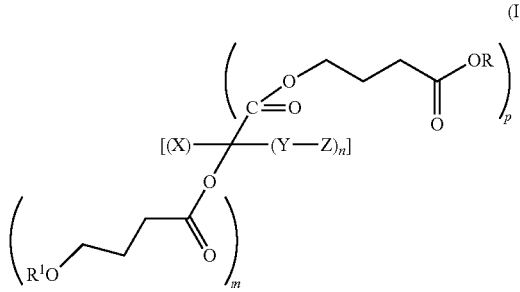

wherein $R^1$ is H or a hydroxyl-protecting group, R is H, $(C_1-C_4)$ alkyl or benzyl, X is a residue of a hydroxy group-containing amino acids, Z is a residue of a hydroxyl group-containing amino acid or a bis(carboxy)amino acid, Y is a moiety covalently linking X and Z, n is 0-1, m is 0 to the number of hydroxy groups on amino acid X, p is 1 to the number of $CO_2H$ groups on the amino acid X or Z, or a pharmaceutically acceptable salt thereof.

Preferably, m, p, q and k are individually 0-5, more preferably O-3, and most preferably 0-2.

In one preferred embodiment of the compound of formula (III), m=p=1, n is 0 and X is glutamic acid, tyrosine, aspartic acid, threonine, or a serine. In another preferred embodiment of the compound of formula (III), m=p=1, n is 1, and Y is $C(O)CH_2CH_2C(O)$ or $C(O)CH=CH(CO)$.

The present invention also provides a compound of formula (IV):

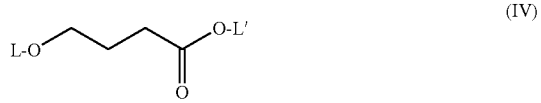

wherein L and L' are individually H, $(C_1-C_6)$alkyl or a hydroxyl protecting group or an organic moiety comprising at least one fatty alcohol, ester or analog thereof. At least one of L and L' is said moiety (the FA moiety). Preferably, the FA moiety is $-(A)(Y)(Z)_n$, and wherein A is $(C_2-C_6)$alkyl, Y is H, OH, $N(R^1)(R^2)(R^3)$ or $[-O(PO_3^-)-A-N(R^1)(R^2)(R^3)]$ wherein $R^1$, $R^2$ and $R^3$ are each $(C_1-C_4)$alkyl or $R^1$ and $R^2$ together with N are a $(C_5-C_7)$heterocyclic ring, optionally substituted with 1 or 2 $N(R^3)$, S, non-peroxide O or a combination thereof; n is 1-2 and Z is XR, wherein X is O, S, NH, $N(CH_3)$, NHC(O) or OC(O) and R is $(C_8-C_{22})$alkyl, optionally substituted with 1-2 double bonds.

Preferably, one of L or L' is $-(A)(Y)(Z)_n$ and the other is H; n=1, XR is $(C_{10}-C_{20})$alkylC(O), $R^1$, $R^2$ and $R^3$ are methyl and/or A is propyl or ethyl. Preferably, when L' is a 2-substituted lecithin moiety, i.e., the $C^2OC(O)R$ moiety of lecithin is replaced by $C^2OC(O)(CH_2)_3OL$ and XR is hexadecanoyloxy; L is not H. Preferably n=1 and $-(A)(Y)(Z)_n$ is $-CH[CH_2Y][CH_2Z]$, e.g., is derived by replacement of the 2'-acyloxyl moiety of lecithin with $L-O(CH_2)_3C(O)-$. When one of L or L' is 1,3-dihexadecanoyloxypropyl-2-yl, the other is not H.

Generally, L and L' are derived from organic polyols, such as glycerol, ethylene glycol, propylene glycol, 2,2'-hydroxy-ethyl ether and the like. The organic moieties L and L' can also be simple fatty acid esters of $C^4$—OH or fatty alcohol esters of $CO_2H$.

The present invention also provides compounds of formula (V):

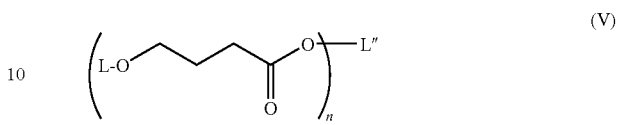

wherein L is defined above, n is 2-6, preferably 2-5, most preferably 2-3, and L" is $(C_2-C_{12})$ alkyl, preferably $(C_3-C_{10})$ alkyl, most preferably $(C_3-C_6)$alkyl, wherein the alkyl chain is optionally interrupted by about 1-3-O— moieties, i.e., is the residue of an alkylene polyol, preferably a 1,ω-alkylene diol such as 1,3-propane diol, or a polyoxyalkylene glycol. Examples of compounds of formula (V) include 1,2,3-tris(4-hydroxy-butyroyoxyl)propane and 1,3-bis(4-acetoxybutyroyoxyl)propane.

The present invention also provides a pharmaceutical composition comprising an effective amount of the compound of formula (I), (II), (III) or (IV), or mixtures thereof in combination with a pharmaceutically acceptable carrier. The pharmaceutical composition of the present invention may be adapted for parenteral, oral, topical or local administration.

The present invention also provides a therapeutic method comprising administering to a mammal afflicted with a pathology or condition ameliorated by GHB, an amount of a compound of formula I, II, III, IV and/or V effective to treat said pathology or condition.

As used herein, the term "effective amount" means that the composition can deliver an amount of GHB to a target cell, tissue or organ effective to accomplish a therapeutic objective, i.e., to alter cellular metabolism or energetics or to ameliorate at least one symptom of one of the pathologies discussed herein.

BRIEF DESCRIPTION OF THE FIGURES

The following drawings from part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

A. Definitions

Figure 1A:
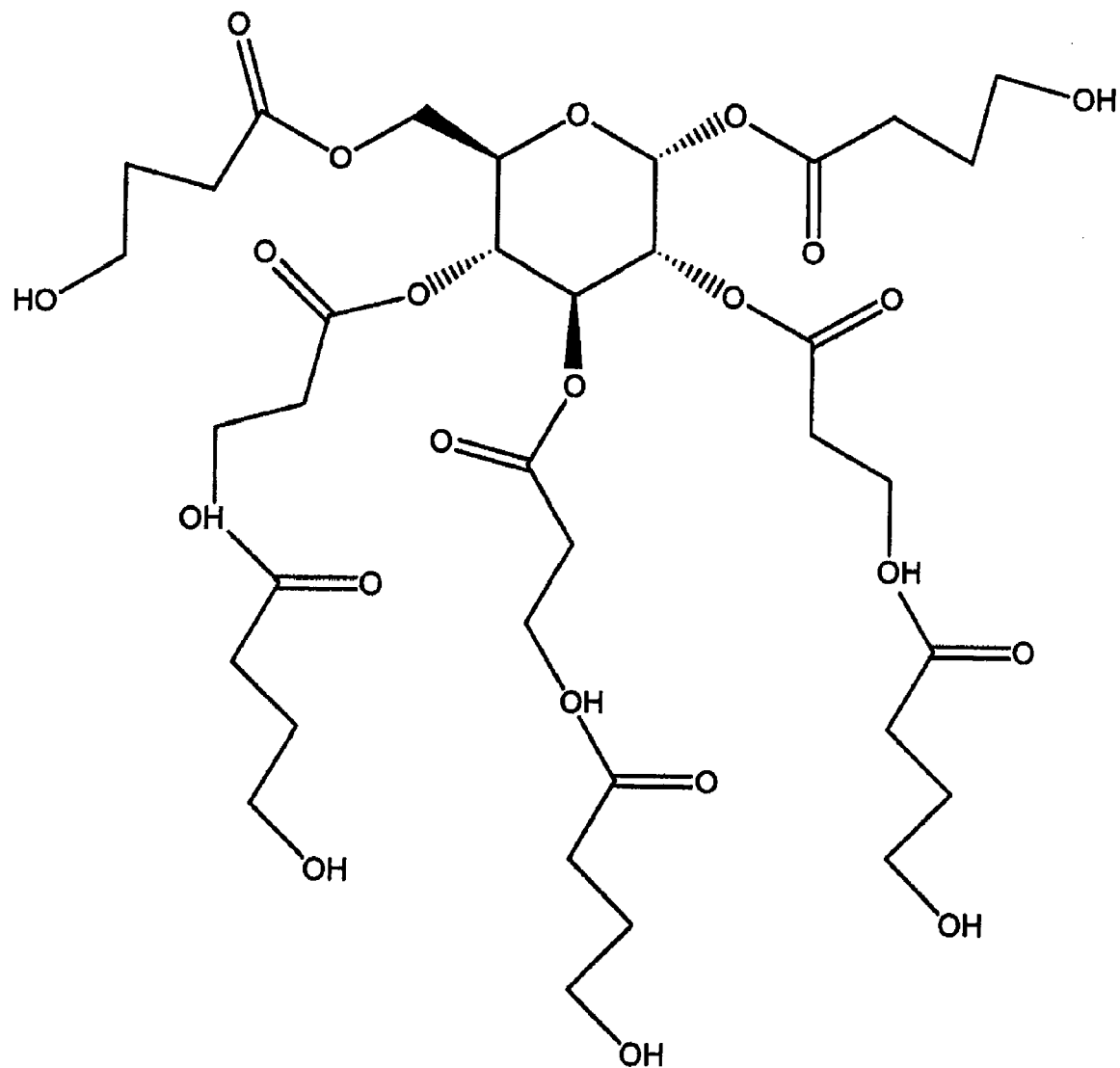
FIG. 1A shows a compound comprising the GHB pentaester of a fully charged hexopyranose.

The term "amino acid" comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "hydroxy amino acid" includes naturally occurring, synthetic and semi-synthetic amino acids, such as serine, threonine, tyrosine and hydroxyproline.

Preferably the amino acids are α-amino acids, most preferably with ω-hydroxyl groups.

The term "carbohydrate" as used herein is defined to include polyhydroxy aldehydes, or polyhydroxy ketones or substances that yield such compounds on hydrolysis. The term "carbohydrate" includes monosaccharides, oligosaccharides, disaccharides, trisaccharides, tetrasaccharides, pentasaccharides, hexasaccharides, polysaccharides, homopolysaccharides, and heteropolysaccharides. The term includes any of the aldoses, as well as glucose, dextrose, mannose, galactose arabinose, xylose, ribose, fructose, sucrose, altrose, allose, idose, gulose, talose, lyxose, threose, erythrose, apiose, and any of the same in acid form. The term also includes deoxy sugars and deoxy-aldoses, including rhamnose and fucose. The term further includes glyceraldehyde, cellulose, starch, glycogen, and amylose. The term also includes carbohydrate derivatives, such as acetals, ketals, acyl esters and the like. Chemically modified polysaccharides such as sucralfate and modified starches are also within the scope of the term. Additional suitable carbohydrates of the present invention may be found in Noller, C., *Chemistry of Organic Compounds,* 2nd ed. (W. B. Saunders Co., 1957).

The term "saccharide" includes monosaccharides, disaccharides, trisaccharides and polysaccharides. The term includes glucose, sucrose, fructose and ribose, as well as deoxy sugars such as deoxyribose and the like. Saccharide derivatives can conveniently be prepared as described in International Patent Applications Publication Numbers WO 96/34005 and 97/03995.

The term "oligopeptide" describes a sequence of 2 to 25 amino acids (e.g. as defined hereinabove) or peptidyl residues. The sequence may be linear, branched or cyclic. For example, a cyclic peptide can be prepared or may result from the formation of disulfide bridges between two cysteine residues in a sequence. An oligopeptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620.

The term "linking moiety" or "linker" as used herein refers to an at least divalent organic molecule that can join two amino acids or oligopeptidyl residues by reaction with functional groups therein. Such moieties include alkane and alkene dicarboxylic acids and diamines.

The term "alkyl" includes branched, straight-chain and cyclic alkyl groups, including (cycloalkyl)alkyl.

A fatty alcohol is a $(C_8-C_{22})$alkanol, preferably a $(C_{10}-C_{20})$ alkanol, optionally comprising 1-3 double bonds; a fatty acid is a $(C_8-C_{22})$alkanoic acid (i.e., $(C_1-C_{11})C(O)OH$), optionally comprising 1-3 double bonds.

The term "hydroxyl protecting group" includes removable hydroxy moiety protecting groups known to the art, such as acid- or base-labile groups such as acetals (THP, (1-ethoxy) ethyl), tris(alkyl)silyl groups ($Me_3$, Si, $(t-Bu(Me_2)Si)$), $(C_2-C_7)$acyl groups (acetyl), as well as groups that can be removed by hydrogenolysis, such as benzyl. See, also, part (C)(a), hereinbelow, which references additional OH protecting groups.

B. Applications

GHB has been shown to be effective in treating narcolepsy and sleep disorders (Lee, 1977; Mamelak, 1977; Hoes, 1980; Scharf, 1985; Scrima, 1990; Gallimberti, 1992; Series, 1992; Lammers, 1993), reducing alcohol craving and alcohol withdrawal symptoms (Gallimberti et al., 1989; Gallimberti et al., 1992; Gessa et al., 1992), reducing opiate withdrawal symptoms (Gallimberti et al., 1994; Gallimberti et al., 1993), reducing pain (U.S. Pat. No. 4,393,236), reducing intracranial pressure in patients (Strong, A., 1984), and increasing growth hormone levels in patients (Gerra et al., 1994; Oyama et al., 1970). The compounds and compositions of the present invention can also be used in the treatment of any of these disorders or conditions in patients.

GHB has been used with other analgesics, neuroleptics, or with a subliminal barbiturate dose for use as an anesthesia. GHB has been used in closed cranio-cerebral trauma and as soporifics (U.S. Pat. No. 5,380,937). Therefore, the compounds of the present invention can also be used in combination with analgesics, neuroleptics or barbiturates for use as an anesthesia. The inventors contemplate the use of the GHB compositions of the present invention as a narcotic, hypnotic, or as a soporific.

The present invention provides compounds and pharmaceutical compositions that can be used in the treatments of hypnosis; narcolepsy (particularly cataplexy); drug abuse; anxiety; cerebrovascular diseases; central nervous system disorders, neurological disorders, including Parkinson's Disease and Alzheimer Disease; Multiple Sclerosis; autism; depression; inflammatory disorders, including those of the bowel, such as irritable bowel disorder, regional illitis, and ulcerative collitis; autoimmune inflammatory disorders; certain endocrine disturbances and diabetes. The present compounds can also be administered for the purpose of tissue protection, including protection following hypoxia/anoxia such as in stroke, organ transplantation, organ preservation, myocardial infarction or ischemia/reperfusion injury; protection following radiation, progeria, or an increased level of intracranial pressure, e.g., due to head trauma. The present compounds can be used to treat other pathologies believed to be caused or exacerbated by lipid peroxidation and/or free radicals, such as pathologies associated with oxidative stress, including normal aging.

C. Availability and Preparation of Compounds of the Present Invention

GHB is available from the Aldrich Chemical Co., Milwaukee, Wis., and can be employed to prepare the compounds within the scope of formula (I) or (II). The GHB compositions of the present invention can be prepared by and administered by any of the means described herein, particularly those described in the section and the examples, or by any means as would be known to those of skill in the art.

A compound of the present invention can be employed as the free acid or alcohol, or as a pharmaceutically acceptable salt or ester thereof. Such salts can be formed from acids or amino groups described herein, by methods available to one or ordinary skill in the art. In cases where compounds are sufficiently basic or acidic to form stable salts with nontoxic organic acids or metal salts, administration of the compounds as salts may be appropriate. Examples of pharmaceutically acceptable salts are organic acid addition salts formed with acids which can form a physiological acceptable anion, for example, tosylate, methanesulfonate, acetate, citrate, malonate, tartarate, succinate, benzoate, ascorbate, α-ketoglutarate, and αglycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. The cations can also be readily exchanged with other metal or organic cations, such as $Ca^+$, $K^+$, $Li^+$, or $(R)_4N^+$ wherein each R is H, phenyl, $(C_1-C_6)$alkyl or hydroxy$(C_1-C_6)$alkyl, i.e., ammonium or hydroxyethyl amine salts.

Hydroxy protecting groups such as esters, ethers, acetals and ketals may be utilized in the present compounds. Useful hydroxy protecting groups are described in Greene, T. W.; Wutz, P. G. M., "Protecting Groups in Organic Synthesis", 2nd ed., John Wiley & Sons, Inc (1991).

a) Preparation of Carbohydrate-GHB Compounds

GHB can be esterified with $(C_1-C_4)$alkanols or the benzyl ester prepared. For ester preparation methods, see S. Ege, *Organic Chemistry*, p. 454-455, 459, 466-467 (D.C. Heath and Co., 1984). See also, Pouillart et al., *Eur. J. Pharm. Sci.*, 7, 93-106 (1998). Then the OH group can be protected by formation of an acetal or by alkanoylation or benzoylation with an alkanoyl or benzoyl chloride or with anhydrides. Other useful acid- and base-labile hydroxy-protecting groups are described in Greene, T. W.; Wutz, P. G. M. "Protecting Groups In Organic Synthesis" second edition, 1991, New York, John Wiley & Sons, Inc.

The ester can be removed and the acid can be activated if necessary, i.e., by formation of an acid chloride or anhydride. For preparation methods for 4-hydroxy-butanoic acid and its derivatives, see, Marvel et al., *J. Am. Chem. Soc.*, 51, 260 (1929); Japanese patent 63174947, German Pat. Nos. 237310, 237308 and 237309.

The activated carboxyl group of GHB can be reacted with the target hydroxyl groups in various sugars via ester bonds, as described, for example, in P. Pouillart et al., *Eur. J. Pharm. Sci.*, 7, 93 (1998), P. R. Pouillart, *Life Sciences*, 63, 1739 (1998); P. Pouillart et al., *J. Pharm. Sci.*, 81, 241 (1992), and references cited therein. Most types of sugars, including triose (or glycerol) tetroses, pentoses and hexoses can be used to make the compounds of the present invention. In the latter two cases, the open chain and ring (pyranoses and furanoses) forms may be used as scaffolds. An example of hexopyranose is depicted in FIG. 1a, where a maximum of 5 GHB molecules can be anchored to each sugar monomer.

The therapeutic potential of these compounds is dependant on the stability of the compounds in various environments. It is contemplated that fully charged GHB compounds can be synthesized from sucrose (containing a furanose and a pyranose ring), glucose and one from any open chain hexose. These compounds may be synthesized by a single step from free GHB or from its lactone.

In a fully charged molecule, i.e, $(GHB)_5$-Sugar, the hydrocarbon chains may provide adequate protection from enzymes present in the digestive tract. These compositions may be susceptible to acid catalyzed hydrolysis, which depends on the steric environments around each ester bond. For example, the 6-OH ester bond will be readily hydrolyzed. These molecules may be viewed as miniature micelles and can be transported into the circulatory system via the fat absorption mechanism.

Figure 1B:
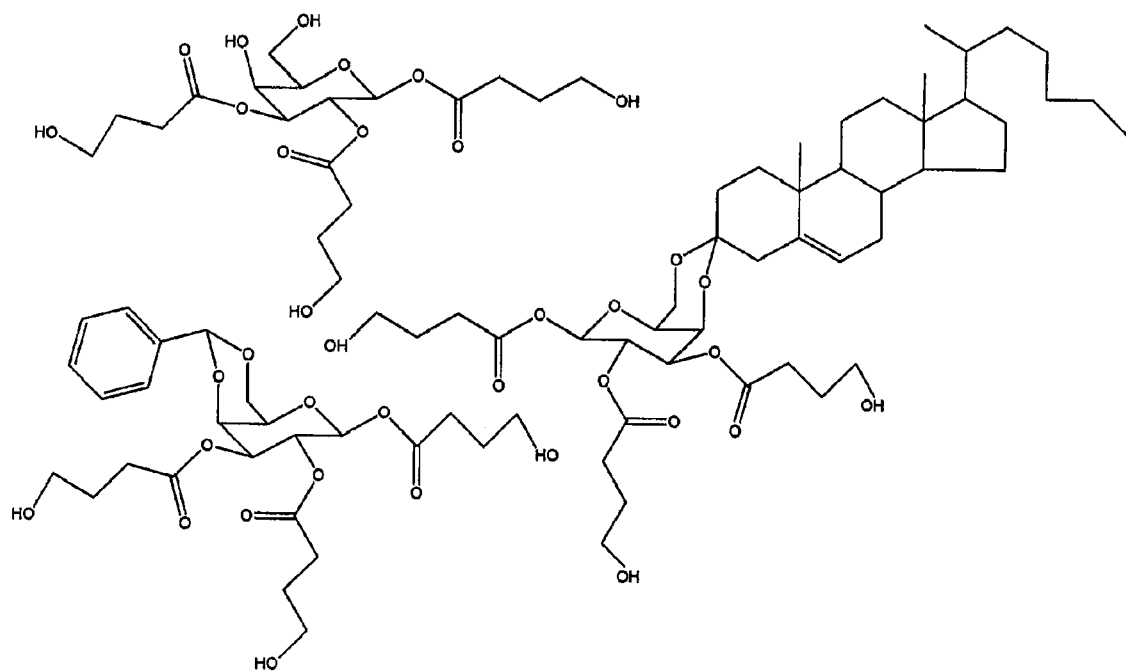
FIG. 1B shows GHB triesters of partially charged hexopyranoses.
Figure 2:
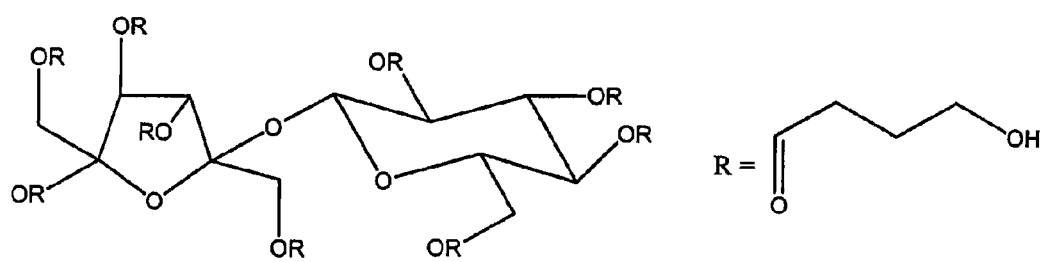
FIG. 2 shows a GHB-sucrose ester.
Figure 3A:
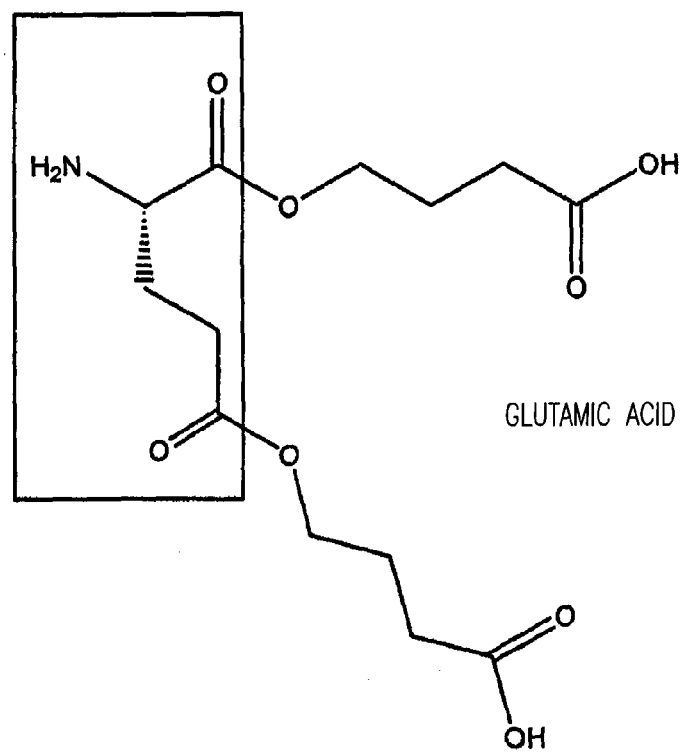
FIG. 3 shows a GHB linked to representative amino acids.
Figure 3B:
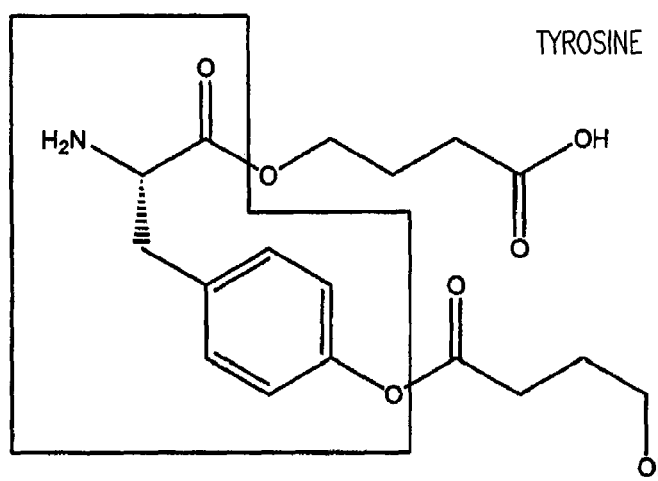
Figure 3C:
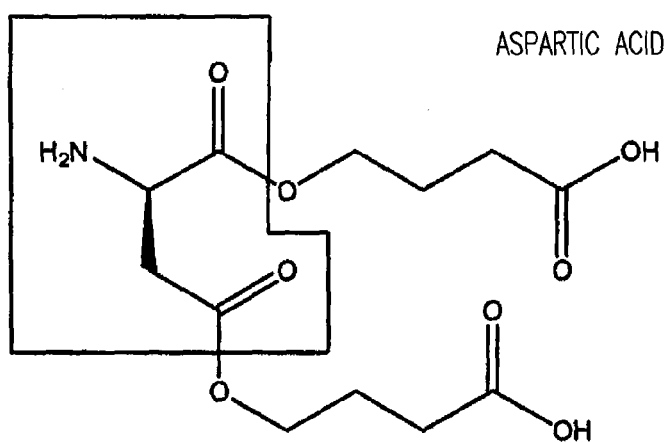
Figure 3D:
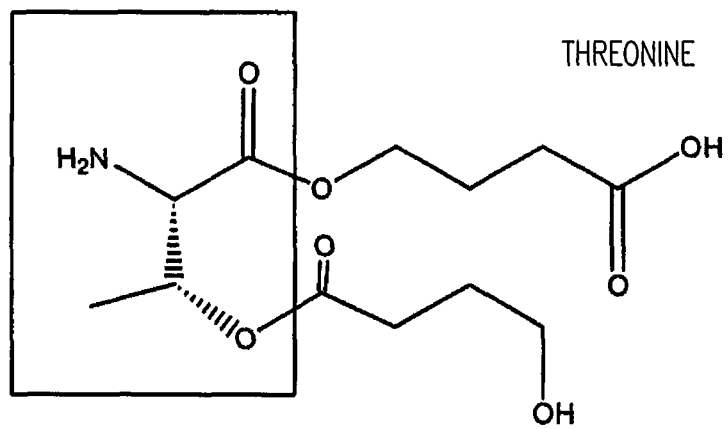
Figure 3E:
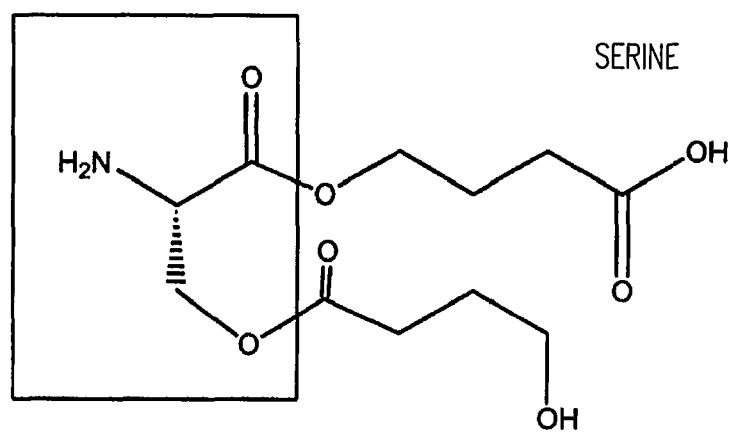

Linking GHB to partially charged sugars may provide for better uptake and delivery of the drug. As seen in FIG. 1b, the depicted compound has only 3-GHBs attached to the sugar. The choice of hydroxyl groups for esterification can be based on the rates of hydrolysis of the corresponding esters so that desired levels of free GHB can be maintained within the cells of the target organ.

Free hydroxyl groups can be used to anchor various groups. Steric shielding of GHB-ester linkages enhances the stability of the compounds in acidic medium. For example, one or more pairs of adjacent OH group groups on the sugar ring can be protected as acetals or as ketals, as taught by Pouillart et al., cited above, using acetals. The ketone can be varied in bulk, in order to shield the ester linkages to a greater or lesser extent. The attachment of lipophilic groups, such as steroids or fatty acids, to GHB via e.g., ketal or acetal linkages, can enhance the transfer across the blood-brain barrier. The use of a ketosteroid or benzaldehyde to form a ketal or acetal is shown in FIG. 1(b). A lipophilic composition may also be useful for delivery of GHB via salves or dermal patches. Free hydroxyl groups of the sugar may also be used to attach a second complementary therapeutic agent to the GHB composition.

b) Preparation of GHB Amino Acid Compounds

Amino acids (AA), serine, threonine, tyrosine, aspartic acid and glutamic acid contain side chains containing OH groups and/or second $CO_2H$ groups that can be coupled to GHB by ester linkages, following N-protection (See FIG. 3). Each of these compounds could be linked to two GHB molecules. Alternatively, the carboxylic acid of GHB can be reacted with an acid-protected amino acid to form the amide from the amine of the amino acid. Because the ester linkages of these compounds have different steric environments, the hydrolysis rates of these compounds in vivo will vary. A significantly slow rate of hydrolysis will be seen with serine and threonine, due to the ester linkages associated with their side chains. For tyrosine, the ester linkage associated with the phenoxy side chain can be very rapidly hydrolyzed. Single amino acid compounds, i.e., $AA-(GHB)_2$ can only deliver 2 GHB molecules, and due to the lack of steric shielding, these compounds may have limited stability in the stomach pH. However, tailored small peptides having 3 to 5 amino acids can significantly improve the quantity of GHB delivered and have enhanced stability.

Figure 4A:
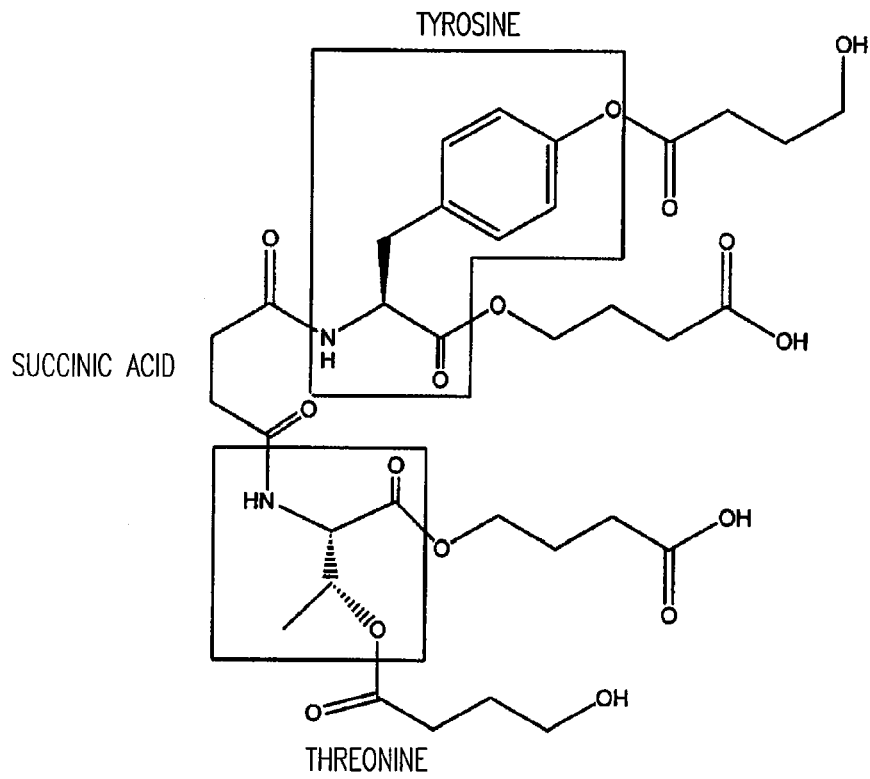
FIG. 4 shows a GHB linked to amino acid conjugates.
Figure 4B:
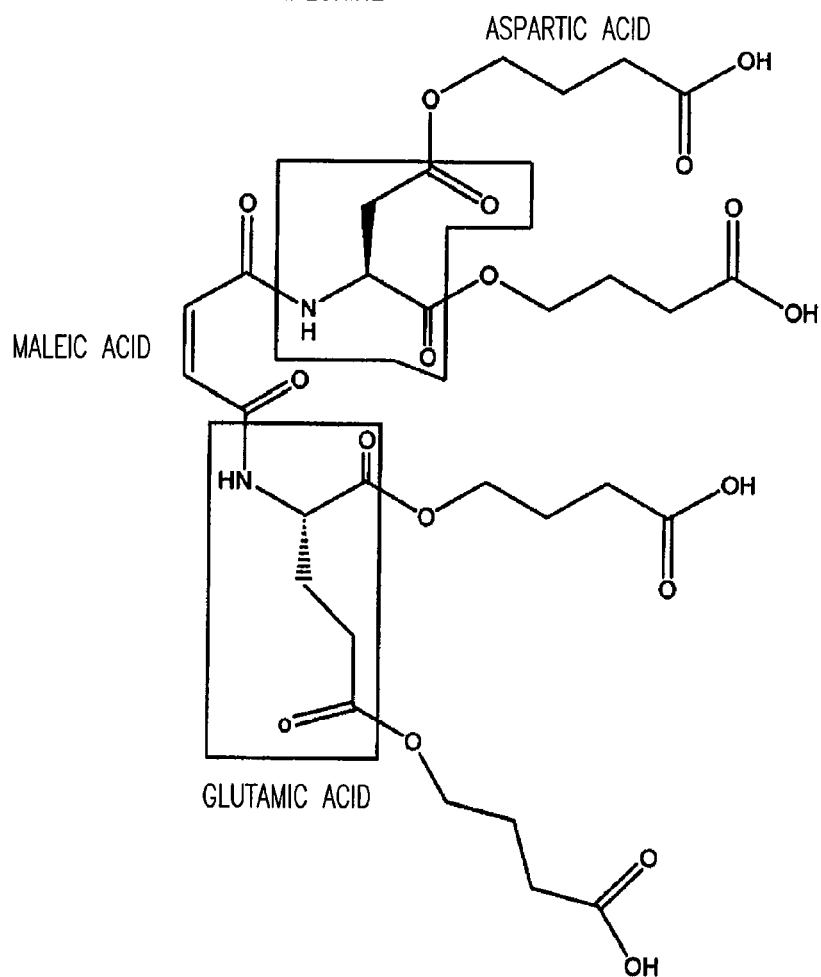

It is contemplated that the compounds of the present invention may comprise two or more amino acids. Such compounds can be constructed by using covalent linking moieties such as succinic acid to couple the amino acids tyrosine and threonine, or using maleic acid to couple aspartic and glutamic acids. Each of these conjugates comprises 4 GHB per molecule, where each ester linkage is in a significantly different steric shielding. (See FIG. 4). As backbones of the compounds, the succinic and maleic acid linkers have significantly different degrees of flexibility. Succinic acid has full rotational freedom, whereas using maleic acid, GHB molecules will be held in a cis orientation. Each compound, having two amide and four ester linkages, can give rise to distinct structural organizations with different stability and cellular uptake.

c) Preparation of Compounds of Formulas (IV) and (V)

Analogs of naturally occurring phospholipids and lipids are known to the art.

The compounds of formula III can be prepared as disclosed in PCT WO 92/03462; U.S. Pat. No. 5,223,263; PCT/US91/04289; or PCT/US94/05855. Lecithin or a sphingolipid can be partially hydrolyzed to yield one or more free OH groups and GHB attached as discussed above.

Compounds of formula (V) can be prepared by the reaction of polyols (L"(OH)$_n$) with 4-halobutyroylchloride, which is then hydrolyzed and the 4-hydroxyl group protected, or the 4-halo group is displaced by L"O⁻ or an equivalent thereof.

D. Administration

The invention provides a pharmaceutical formulation comprising a compound of formula (I), (II), or (III), together with one or more pharmaceutically acceptable carriers therefor and, optionally, other therapeutic and/or prophylactic ingredients. The cations and carrier(s) must be "acceptable" in the sense of being compatible with the other ingredients of the formulation and not deleterious to the recipient thereof, i.e., they do not produce an adverse, allergic, or other untoward reaction when administered to an animal, or a human, at appropriate levels.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal, transdermal or sublingual) administration. The formulations may, where appropriate, be conveniently presented in discrete unit dosage forms, by bringing the active compound into association with liquid carriers, solid matrices, semi-solid carriers, finely divided solid carriers or combinations thereof, and then, if necessary, shaping the product into the desired delivery system.

a) Parenteral Administration and Dosage Forms

The active compounds of the invention may be formulated for parenteral administration, e.g., formulated for injection via intravenous, intraarterial, intramuscular, subcutaneous, intralesional, intraperitoneal or other parenteral routes. The preparation of an aqueous composition that contains a GHB agent as an active component or ingredient will be known to those of skill in the art in light of the present disclosure.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions. The compounds of the invention may be lyophilized for more ready formulation into a desired vehicle where appropriate. For injection or infusion, the active agent can optionally be encapsulated in liposomes. In all cases, the ultimate dosage form should be sterile, fluid and stable under the conditions of manufacture and storage.

The liquid carrier or vehicle can be a solvent or liquid dispersion medium comprising, for example, water, ethanol, glycerol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, by the use of surfactants, or by the use of a substance, such as lecithin (e.g., a coating). Solutions of the active compounds as free acid or pharmacologically acceptable salts can be prepared in water suitably mixed with hydroxypropylcellulose and/or a pharmaceutically acceptable surfactant. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered, pyrogen-free solution thereof. The preparation of more, or highly, concentrated solutions for direct injection is contemplated, where the use of DMSO as solvent (although DMSO may not now be a permitted human drug) is envisioned to result in extremely rapid penetration, delivering high concentrations of the active agents to a small area.

The compounds according to the invention may be presented in unit dose form in ampules, pre-filled syringes, small volume infusion containers, multi-dose containers with an added preservative, or indwelling pumps or dispensers, or in devices which allow for sustained release of the compounds.

The active GHB agent may be included within a therapeutic composition to comprise about 0.1 to about 100 grams GHB per unit dosage form, and multiple doses can also be administered. As an example, one dosage could be dissolved in 1 ml of isotonic NaCl solution and either added to 1000 ml of fluid or injected at the proposed site of infusion (see, for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

b) Oral and Topical Administration and Dosage Forms

In addition to the compounds formulated for parenteral administration, other pharmaceutically acceptable forms include, e.g., tablets or other solids; liposomal formulations; time release capsules; and any other form currently used, including creams or lotions, which then may be admixed with an aqueous medium for oral administration.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the active ingredient from a chewing gum. The active ingredient may also be presented as a bolus, syrup, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

The tablets, troches, pills, capsules and the like may also contain the following: a binder, natural as gum tragacanth, acacia, cornstarch, or gelatin or synthetic as polyvinyl acetate; excipients, such as dicalcium phosphate; a disintegrating agent, such as corn starch, potato starch, alginic acid and the like; a lubricant, such as magnesium stearate; and a sweetening agent, such as sucrose, lactose, aspartame or saccharin may be added or a natural or synthetic flavoring agent.

When the dosage unit form is a capsule for admixing with a specific volume of an aqueous medium, it may contain, in addition to materials of the above type, a liquid carrier, such as vegetable oil or a polyethylene glycol. Various other materials may be present as coatings or to otherwise modify the physical form of the dosage unit. For instance, tablets, pills, or capsules may be coated with gelatin, wax, shellac, sugar, natural or synthetic polymers, or both. A syrup or elixir may contain the active compounds, sucrose or fructose as a sweetening agent, a preservative, a dye and/or a flavoring. Of course, any material used in preparing any unit dosage form should be pharmaceutically acceptable and substantially non-toxic in the amounts employed.

Such compositions and preparations should contain at least 0.1% of the active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The GHB-containing agent may be packaged separately from or in combination with the excipients, salts, flavorings or any other components described herein, to be admixed with an aqueous medium in the case of oral or injectable formulations, or they may be incorporated directly with the food (i.e., a beverage, candy bar or cake) of the diet.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. Examples of useful dermatological compositions which can be used to deliver the compounds of formula I, II, or III to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful solid carriers for dermatological compositions include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Ointments, pastes, gels, lotions, soaps and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Thickeners such as synthetic polymers, fatty acids, fatty acid salts and esters, fatty alcohols, modified celluloses or modified mineral materials can be employed.

For systemic administration or as topical administration to the epidermis, compound(s) of formula (I), formula (II), or formula (III) may be formulated as the active ingredient of a transdermal patch. Suitable transdermal delivery systems are disclosed, for example, in A. Fisher et al. (U.S. Pat. No. 4,788,603), Chien et al. (U.S. Pat. No. 5,145,682) or R. Bawa et al. (U.S. Pat. Nos. 4,931,279, 4,668,506 and 4,713,224). The active ingredient can also be delivered via iontophoresis, e.g., as disclosed in U.S. Pat. Nos. 4,140,122, 4,383,529, or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to provide sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered form an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhaler or insufflator.

For intra-nasal administration, the compounds of the invention may be administered via a liquid spray, such as via a plastic bottle atomizer. Typical of these are the Mistometer® (Wintrop) and the Medihaler® (Riker). Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and lightly buffered to maintain a pH of 5.5 to 6.5, though other pH ranges disclosed herein the specific example, such as pH 3 to about pH 9, or pH 6 to about 7.5, are contemplated. In addition, preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

c) Dosages

A good safety profile for GHB consumption, when used long term for treatment of narcolepsy, has been reported. Patients have been safely treated for many years with GHB without development of tolerance (Scharf, 1985). Clinical laboratory tests carried out periodically on many patients have not indicated organ or other toxicities (Lammers, 1993; Scrima, 1990; Scharf, 1985; Mamelak, 1977; Mamelak; 1979; Gallimberti, 1989; Gallimberti, 1992; Gessa, 1992).

In the healthy volunteers study, the pharmacokinetics of three rising GHB doses (12.5, 25, and 50 mg/kg) were investigated. These findings indicate that both the oral absorption and elimination processes of GHB were capacity-limited though the degree of dose dependency was moderate (Palatini et al., 1993).

GHB has typically been administered in clinical trials as an oral solution (Lee, 1977; Mamelak, 1977; Hoes, 1980; Scharf, 1985; Scrima, 1990; Gallimberti, 1992; Series, 1992; Lammers, 1993). When used as an oral solution, the dosages have ranged from 20-45 milligrams per kilogram body weight, twice daily. (Mamelak, 1977.)

It will be appreciated that the amount of the compound of formula (I), (II), (III), (IV) or (V) required for use in treatment will vary not only with the particular compound selected but also with the route of administration, the severity of the condition being treated and the age and condition of the patient and will be ultimately at the discretion of the attendant physician or clinician.

Useful dosages of the compounds of formula (I), (II), (III), (IV) or (V) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I), (II), (III), (IV) or (V) in a liquid composition, such as a lotion, will be from about 0.01-25 wt-%, preferably from about 0.5-10 wt-%. The concentration in a semi-solid or solid composition such as a gel or a powder will be about 0.01-15 wt-%, preferably about 0.5-2.5 wt-%.

In general, however, a suitable dose will be in the range of from about 0.05 to 50 gm per day; or preferably from about 0.05 to about 500 mg per kilogram body weight of the recipient per day, preferably in the range of 0.1 to 200 mg/kg/day.

The compound is conveniently administered in unit dosage form; for example, containing 0.1-20 g, conveniently 1-7.5 g, or more conveniently, 2-5 g of active ingredient per unit dosage form.

The total daily dose, i.e., of about 0.05-50 g, may be administered for about 1-4 months, or longer, as needed.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

EXAMPLE 1

Preparation of 1,3-Bis(4-bromobutyroyl)propane (VII)

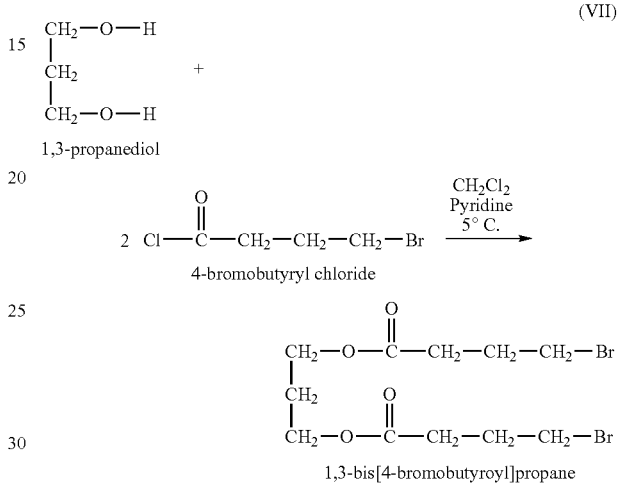

A 500 ml round-bottomed flask was charged with 19.4 ml of pyridine in 150 ml of dichloromethane (CH$_2$Cl$_2$), and stirring initiated as the solution was cooled to 0° C. Propane-1,3-diol (8.0 g) was added, and stirring continued. A mixture of 26.4 ml of 4-bromobutyroyl chloride in 75 ml CH$_2$Cl$_2$ was added dropwise to the stirred pyridine/CH$_2$Cl$_2$ and stirring continued for 5 hrs at 0° C. The reaction mixture was washed with 300 ml H$_2$O, the organic layer was isolated and washed with 100 ml in HCl aq, 100 ml NaCl aq and dried over MgSO$_4$ (anhydrous). The solvents were removed in vacuo to yield the product (VII) as a translucent low viscosity oil.

EXAMPLE 2

Preparation of 1,3-Bis(4-acetoxybutyroyl)propane (VIII)

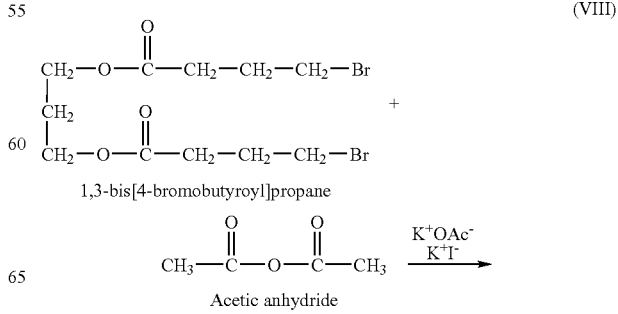

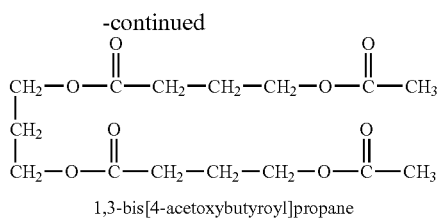

1,3-bis[4-acetoxybutyroyl]propane

A solution of 20.6 g potassium acetate and 3.49 g potassium iodide in 306 ml acetic anhydride was stirred and the product (VII) of Ex. 1 added. The reaction mixture was refluxed with stirring for 12-16 hrs, then cooled to 25° C. and diluted with 100 ml EtOAc. The reaction mixture was filtered, and the filtrate concentrated in vacuo. Ethyl acetate (400 ml) was added and the resultant solution was washed with 2×200 ml of 50% aq. NaHCl$_3$. The organic layer was isolated, dried (MgSO$_4$ an.), filtered and concentrated in vacuo. Purification by flash chromatography yielded product (VIII) in 66.3% yield as a viscous light yellow oil (93% pure).

REFERENCES

Bedard et al., *Clin. Neuropharmacol.*, 12(1) 29 (1989)
Broughton and Mamelak, *Can. J. Neur. Sci.*, 7, 23 (1980)
Gallimberti et al., *Lancet*, 2(8666), 787 (1989)
Gallimberti et al., *Alcohol Clin. Exp. Res.*, 16(4) 673 (1992)
Gallimberti et al., *Neuropsychopharmacology*, 9(1) 77 (1993)
Gallimberti et al., *Eur. Arch. Psychiatry Clin. Neurosci.*, 244 (3) 113 (1994)
Gerra et al., *Int. Clin. Psychopharmacol.*, 9(3) 211 (1994)
Gessa et al., *Clin. Neuropharmacol.*, 15 Suppl. 1 Pt. A 303A (1992)
Grove-White and Kelman, *Br. J. Anaesth*, 43(2) 110 (1971)
Hasenbos and Gielen, *Anaesthesia*, 40(10) 977 (1985)
Hoes et al., *Encephale*, 6(1) 93 (1980)
Laborit, *Laboratoire d'Eutonologie, Hopital Boucicaut* Paris 15 France, 1973
Ladinsky et al., *Naunyn Schmiedebergs Arch Pharmacol.*, 322(1) 42 (1983)
Lammers et al., *Sleep*, 16(3) 216 (1993)
Lapierre et al., *Sleep*, 13(1) 24 (1990)
Lee, *Biochem Med.*, 17(3) 284 (1977)
Mamelak et al., *Lancet*, 2(7824) 328 (1973)
Mamelak et al., *Biol. Psychiatry*, 12(2) 273 (1977)
Mamelak et al., *Biol. Psychiatry*, 14(5) 821 (1979)
Oyama et al., *Br. J. Anaesth.*, 42(12) 1105 (1970)
Palatini et al., *Eur. J. Clin. Pharmacol.*, 45(4) 353 (1993)
Scharf et al., *J. Clin. Psychiatry*, 46(6) 222 (1985)
Scharf et al., *Am. Fam. Phys.*, 143 (1988)
Scrima et al., *Sleep*, 13(6) 479 (1990)
Series et al., *Am. Rev. Respir. Dis.*, 145(6) 1378 (1992)
Scharf et al., *J. Clin Psychiatry*, 46(6) 222 (1985)
Snead and Morley, *Brain Res.*, 227(4) 579 (1981)
Stock et al., *Naunyn Schmiedebergs Arch Pharmacol.*, 278(4) 347 (1973)
Strong, *Lancet*, 1(8389) 1304 (1984)
Yamada et al., *Electroencephalogr. Clin. Neurophysiol.*, 22(6) 558 (1967)

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of the formula (III):

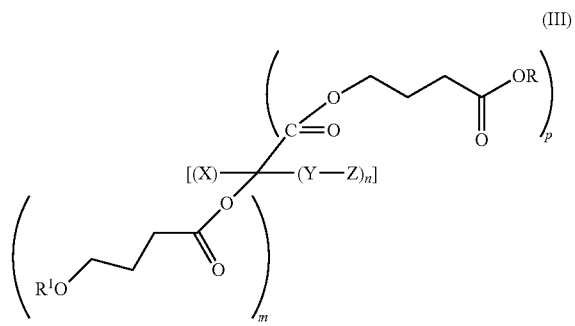

wherein $R^1$ is H or a hydroxyl-protecting group, R is H, $(C_1-C_4)$alkyl or benzyl, X is a residue of a naturally occurring hydroxy group-containing α-amino acid or a naturally occurring bis(carboxy) group containing amino acid, Z is the residue of a naturally occurring hydroxy group-containing α-amino acid or a naturally occurring bis(carboxy) group-containing amino acid, Y is a moiety covalently linking X and Z, n is 0-1, m is 0 to the number of available hydroxy groups in amino acid X and Z, p is 1 to the number of available CO$_2$H groups on the amino acid X and Z, or a pharmaceutically acceptable salt thereof.

2. The compound of claim 1 wherein each of m and p are 2 and n is 1.

3. The compound of claim 1 wherein m is 0, n is 1 and p is 4.

4. The compound of claim 1 wherein n =0, m =0, p =2 and X is the residue of glutamic acid or tyrosine.

5. The compound of claim 1 wherein m=p=1, n is 0 and X is the residue of tyrosine, threonine, or serine.

6. The compound of claim 1, 2 or 3 wherein Y is C(O) CH$_2$CH$_2$C(O) or C(O)CH=CH(CO).

7. A compound of formula (IV):

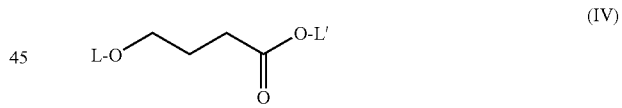

wherein L and L' are individually H, $(C_1-C_6)$alkyl or a hydroxyl protecting group, wherein at least one of L' or L is -(A)(Y)(Z)$_n$, wherein A is $(C_1-C_6)$alkyl, Y is H, OH, N(R$^1$)(R$^2$)(R$^3$) or (O(PO$_3^{31}$)-AN(R$^1$)(R$^2$)(R$^3$,), wherein R$^1$, R$^2$ and R$^3$ are each $(C_1-C_4)$alkyl or R$^1$ and R$^2$ together with N are a $(C_5-C_7)$heterocyclic ring, optionally substituted with 1 or 2 N(R$^3$), S, non-peroxide O or a combination thereof; n is 1-2 and Z is XR, wherein X is O, S, NH, N(CH$_3$), NHC(O) or OC(O) and R is $(C_8-C_{22})$alkyl, optionally substituted with 1-2 double bonds, or a pharmaceutically acceptable salt thereof, with the proviso that when one of L or L' is 1,3-dihexadecanoyloxyprop-2-yl, the other is not H.

8. The compound of claim 7 wherein L' is -(A)(Y)(Z)$_n$ and L is H, $(C_1-C_6)$alkyl or a hydroxyl protecting group.

9. The compound of claim 7 or 8 wherein X is OC(O).

10. The compound of claim 7 wherein R is $(C_{10}-C_{22})$alkyl.

11. The compound of claim 7 or 8 wherein Y is —O(PO$_3^{31}$) CH$_2$CH$_2$N(CH$_3$)$_3^{30}$.

12. The compound of claim 8 or 10 wherein $-(A)(Y)(Z)_n$ is $-CH[CH_2Y][CH_2Z]$.

13. A method for treating a mammal afflicted with a condition or pathology amenable to treatment by gamma-hydroxy butyrate (GHB) comprising administering to said mammal an effective amount of a compound of formula (IV):

(IV)

wherein L and L' are individually H, $(C_1-C_6)$alkyl or a hydroxyl protecting group, wherein at least one of L' or L is $-(A)(Y)(Z)_n$, wherein A is $(C_1-C_6)$alkyl, Y is H, OH, $N(R^1)(R^2)(R^3)$ or $O(PO_3^{31})-AN(R^1)(R^2)(R^3)$, wherein $R^1$, $R^2$ and $R^3$ are each $(C_1-C_4)$alkyl or $R^1$ and $R^2$ together with N are a $(C_5-C_7)$heterocyclic ring, optionally substituted with 1 or 2 $N(R^3)$, S, non-peroxide O or a combination thereof; n is 1-2 and Z is XR, wherein X is O, S, NH, $N(CH_3)$, NHC(O) or OC(O) and R is $(C_8-C_{22})$alkyl, optionally substituted with 1-2 double bonds, or a pharmaceutically acceptable salt thereof, with the proviso that when one of L or L' is 1,3-dihexdecanoyloxyprop-2-yl, the other is not H.

14. A compound of the formula (I):

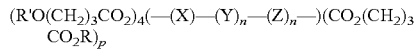

Wherein R' is H or a hydroxyl-protecting group, R is H, $(C_1-C_4)$alkyl or benzyl, X and Z are each residues of a naturally occurring hydroxy group-containing α-amino acid or a naturally occurring bis(carboxy)amino acid, Y is a moiety covalently linking X and Z, n is 0-1, m is 0 to the number of available hydroxy groups on amino acid X and Z, p is 0 to the number of available $CO_2H$ groups on amino acids X and Z, with the proviso that both m and p are not zero, or a pharmaceutically acceptable salt thereof.

15. A method for treating a mammal afflicted with a condition or pathology amenable to treatment by gamma-hydroxy butyrate (GHB) comprising administering to said mammal an effective amount of a compound of the formula (I):

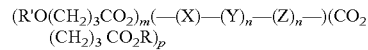

wherein R' is H or a hydroxyl-protecting group, R is H, $(C_1-C_4)$alkyl or benzyl, X and Z are each residues of a naturally occurring hydroxy group-containing α-amino acid or a naturally occurring bis(carboxy)amino acid, Y is a moiety covalently linking X and Z, n is 0-1, m is 0 to the number of available hydroxy groups on amino acid X and Z, p is 0 to the number of available $CO_2H$ groups on amino acids X and Z, with the proviso that both m and p are not zero, or a pharmaceutically acceptable salt thereof.

* * * * *

UNITED STATES PATENT AND TRADEMARK OFFICE
CERTIFICATE OF CORRECTION

PATENT NO. : 8,778,301 B2  
APPLICATION NO. : 12/465069  
DATED : July 15, 2014  
INVENTOR(S) : Mamelak et al.

It is certified that error appears in the above-identified patent and that said Letters Patent is hereby corrected as shown below:

On the title page, in column 2, under "Other Publications", line 22, delete "Hydroxybutric" and insert --Hydroxybutyric--, therefor On title page 2, in column 2, under "Other Publications", line 11, delete "Obsturctive" and insert --Obstructive--, therefor In the Specification:

In column 3, line 27, delete "O-3," and insert --0-3,--, therefor

In column 3, line 63, delete "L-O(CH$_2$)$_3$C(O)-." and insert --L-O(CH$_2$)$_3$C(O)O-.--, therefor In the Claims:

In column 16, line 52, in Claim 7, delete "(O(PO$_3^{31}$)-AN(R$^1$)(R$^2$)(R$^3$,)," and insert --(O(PO$^-_3$)-AN(R$^1$)(R$^2$)(R$^3$),--, therefor In column 16, line 66-67, in Claim 11, delete "-O(PO$_3^{31}$)CH$_2$CH$_2$N(CH$_3$)$_3^{30}$." and insert -- -O(PO$_3^-$)CH$_2$CH$_2$N(CH$_3$)$_3^+$.--, therefor Signed and Sealed this  
Fourteenth Day of October, 2014

Michelle K. Lee  
*Deputy Director of the United States Patent and Trademark Office*